US009579617B2

(12) United States Patent
Churchfield et al.

(10) Patent No.: US 9,579,617 B2
(45) Date of Patent: Feb. 28, 2017

(54) AQUEOUS DISPERSION OF FATTY AMIDE

(71) Applicants: Rohm and Haas Company, Philadelphia, PA (US); Dow Global Technologies LLC, Midland, MI (US)

(72) Inventors: Mechelle Ann Churchfield, Midland, MI (US); Timothy J. Young, Bay City, MI (US); Mai Chen, Chicago, IL (US); Thomas L. Tomczak, Saginaw, MI (US)

(73) Assignees: DOW GLOBAL TECHNOLOGIES LLC, Midland, MI (US); ROHM AND HAAS COMPANY, Philadelphia, PA (US)

( * ) Notice: Subject to any disclaimer, the term of this patent is extended or adjusted under 35 U.S.C. 154(b) by 0 days.

(21) Appl. No.: 14/655,549

(22) PCT Filed: Dec. 5, 2013

(86) PCT No.: PCT/US2013/073240
§ 371 (c)(1),
(2) Date: Jun. 25, 2015

(87) PCT Pub. No.: WO2014/105379
PCT Pub. Date: Jul. 3, 2014

(65) Prior Publication Data
US 2015/0352509 A1 Dec. 10, 2015

Related U.S. Application Data

(60) Provisional application No. 61/746,741, filed on Dec. 28, 2012.

(51) Int. Cl.
*B01F 17/00* (2006.01)
*C07C 233/09* (2006.01)

(52) U.S. Cl.
CPC ......... *B01F 17/0092* (2013.01); *C07C 233/09* (2013.01)

(58) Field of Classification Search
CPC .................... B01F 17/0092; C07C 233/09
See application file for complete search history.

(56) References Cited

U.S. PATENT DOCUMENTS

| 3,811,830 | A | * | 5/1974 | DeMarco | ................ A61K 8/06 8/405 |
| 4,015,999 | A | * | 4/1977 | Robertson | ........... C09B 67/0092 106/419 |
| 4,024,097 | A | * | 5/1977 | Slovinsky | ................ C08F 2/32 524/723 |
| 5,474,638 | A | * | 12/1995 | Kohlhammer | ......... C09J 133/06 156/308.2 |
| 7,361,694 | B2 | | 4/2008 | Strandburg et al. | |
| 8,349,301 | B2 | * | 1/2013 | Wells | ................... A61K 8/0295 424/70.19 |
| 2005/0100754 | A1 | | 5/2005 | Moncla et al. | |
| 2005/0173348 | A1 | | 8/2005 | Drake | |
| 2005/0271888 | A1 | | 12/2005 | Moncla et al. | |
| 2009/0233825 | A1 | * | 9/2009 | Giles | .................... A61K 8/0295 510/123 |
| 2012/0077026 | A1 | | 3/2012 | Igarashi et al. | |
| 2014/0093740 | A1 | * | 4/2014 | Chen | ..................... C09J 133/06 428/476.3 |
| 2015/0352509 | A1 | * | 12/2015 | Churchfield | ........ B01F 17/0092 516/77 |
| 2015/0361312 | A1 | * | 12/2015 | Chen | ........................ C08K 5/20 428/522 |

FOREIGN PATENT DOCUMENTS

| WO | 9820119 A1 | 5/1998 |
| WO | 0220684 A2 | 3/2002 |
| WO | 02090474 A1 | 11/2002 |
| WO | 2008033975 A1 | 3/2008 |
| WO | 2010030196 A1 | 3/2010 |
| WO | 2011053904 A1 | 5/2011 |
| WO | 2012158601 A1 | 11/2012 |

* cited by examiner

*Primary Examiner* — Michael A Salvitti
(74) *Attorney, Agent, or Firm* — Carl Hemenway

(57) ABSTRACT

A composition is provided comprising dispersed particles in an aqueous medium, wherein said dispersed particles comprise fatty amide and one or more fatty acid, wherein 50 mole % or more of said fatty acid in is the carboxylate form, and wherein the weight ratio of said fatty amide to said fatty acid is from 0.12:1 to 2.3:1. Also provided is method of making that composition, comprising the step of applying shear to a mixture that comprises said fatty amide, said fatty acid, and water, wherein said applying shear is performed at a temperature above 59° C., and wherein the amount of water in said mixture is 70% or less by weight based on the weight of said mixture.

20 Claims, No Drawings

AQUEOUS DISPERSION OF FATTY AMIDE

Fatty amide is useful for a variety of purposes, including, for example, as a slip aid additive for polyolefins. It would be desirable to provide fatty amide as a stable dispersion in an aqueous medium. Fatty amide is not soluble in water, and so it cannot be included in waterborne compositions. The ability to provide such a dispersion in water would enable fatty amide to be included in waterborne compositions. In order for the dispersed particles to carry a useful amount of fatty amide, the dispersed particles should contain more than 10% fatty amide by weight based on the weight of the particles. However, in the past it was not known how to make such a dispersion with stable shelf life.

WO 2011/053904 provides methods of making an aqueous dispersion of alkyd resin. It is desired to find a method of making a dispersion in which the dispersed particles contain fatty amide.

The following is a statement of the invention.

The first aspect of the present invention is a composition comprising dispersed particles in an aqueous medium, wherein said dispersed particles comprise fatty amide and one or more fatty acid, wherein 50 mole % or more of said fatty acid in is the carboxylate form, and wherein the weight ratio of said fatty amide to said fatty acid is from 0.12:1 to 2.3:1.

The second aspect of the present invention is a method of making that composition, comprising the step of applying shear to a mixture that comprises said fatty amide, said fatty acid, and water, wherein said applying shear is performed at a temperature above 59° C., and wherein the amount of water in said mixture is 70% or less by weight based on the weight of said mixture.

The following is a detailed description of the invention.

As used herein, the following terms have the designated definitions, unless the context clearly indicates otherwise.

As used herein, a dispersion is a composition that contains discrete particles that are distributed throughout a continuous liquid medium. The distributed particles are said to be dispersed. Each discrete particle may be solid, liquid, or a combination thereof. The continuous liquid medium is liquid over a range of temperature that includes 10° C. to 40° C. The continuous liquid medium is an aqueous medium if the composition of the continuous liquid medium contains water in the amount of 60% or more by weight based on the weight of the continuous liquid medium.

The composition of a collection of particles is considered herein to be uniform if the composition does not vary substantially among the particles.

As used herein, a fatty acid has the chemical formula $R^1$—COOH, where $R^1$ is a substituted or unsubstituted hydrocarbyl group that contains 8 or more carbon atoms. As used herein, the term fatty acid is meant to include both the carboxyl form $R^1$—COOH and the carboxylate form $R^1$—COO$^\ominus$. The carboxylate form may be in solution or in a salt.

As used herein, a fatty amide has the chemical formula $R^2$—C(O)NHR$^3$, where $R^2$ is a substituted or unsubstituted hydrocarbyl group that contains 8 or more carbon atoms, and where $R^3$ is selected from the following:
(I) $R^3$ is hydrogen ("type I" fatty amide)
(II) $R^3$ is an aliphatic unsubstituted hydrocarbyl group ("type II" fatty amide), or
(III) $R^3$ has the structure —CH$_2$CH$_2$—NHC(O)—R$^4$, where $R^4$ is a substituted or unsubstituted hydrocarbyl group that contains 8 or more carbon atoms ("type III" fatty amide).

Erucamide has the chemical formula $CH_3$—$(CH_2)_7$—CH═CH—$(CH_2)_{11}$—C(O)—NH$_2$. Erucic acid has the chemical formula $CH_3$—$(CH_2)_7$—CH═CH—$(CH_2)_{11}$—C(O)—OH.

As used herein, applying shear to a liquid composition means to place a continuous sample of the liquid in a mechanical configuration in which one portion of the sample of the liquid moves relative to another portion of the sample of the liquid.

As used herein, a neutralizing agent is a base of sufficient strength to convert the fatty acid used in the composition of the present invention to the carboxylate form.

As used herein, the statement that a ratio is "X:1 or higher" means that the ratio is Y:1, where Y is equal to or higher than X. For example, a ratio that is said to be "3:1 or higher" could be 3:1 or 4:1 or 100:1 but could not be 2.9:1. Similarly, the statement that a ratio is "W:1 or lower" means that the ratio is Z:1, where Z is equal to or lower than W. For example, a ratio that is said to be "20:1 or lower" could be 20:1 or 19:1 or 0.15:1 but could not be 21:1.

As used herein, "room temperature" is approximately 25° C.

The present invention involves a continuous liquid medium that is an aqueous medium. Preferably, the amount of water in the aqueous medium is, by weight based on the weight of the aqueous medium, 70% or more; more preferably 80% or more; more preferably 90% or more.

In the present invention, a dispersed phase is dispersed in the aqueous medium. Preferably, the median diameter of the dispersed particles on a volume basis is 50 micrometers or less; more preferably 20 micrometers or less; more preferably 10 micrometers or less; more preferably 5 micrometers or less. Preferably, the median diameter of the dispersed particles on a volume basis is 0.01 micrometers or more; more preferably 0.02 micrometers or more; more preferably 0.05 micrometers or more; more preferably 0.1 micrometers or more.

In preferred fatty amides, $R^2$ is an unsubstituted hydrocarbyl group having 12 or more carbon atoms; more preferably 16 or more carbon atoms; more preferably 18 or more carbon atoms. In preferred fatty amides, $R^2$ is an unsubstituted hydrocarbyl group having 30 or fewer carbon atoms, more preferably 25 or fewer.

Among type III fatty amides, preferably $R^4$ is an unsubstituted hydrocarbyl group having 12 or more carbon atoms; more preferably 16 or more carbon atoms; more preferably 18 or more carbon atoms. Among type III fatty amides, preferably $R^4$ is an unsubstituted hydrocarbyl group having 30 or fewer carbon atoms, more preferably 25 or fewer. Among type II fatty amides, preferably $R^3$ has 12 or more carbon atoms; more preferably 16 or more carbon atoms; more preferably 18 or more carbon atoms. Among type II fatty amides, preferably $R^3$ has 30 or fewer carbon atoms, more preferably 25 or fewer.

Type I fatty amides are preferred. Preferred fatty amides are erucamide and oleamide; most preferred is erucamide.

Preferably, the composition of the dispersed particles is uniform.

Preferably, the amount of fatty amide in the particles is, by weight based on the weight of the particles, 60% or less; more preferably 55% or less. Preferably, the amount of fatty amide in the particles is, by weight based on the weight of the particles, more than 10%; more preferably 15% or more.

Preferably, the amount of fatty acid in the particles is, by weight based on the weight of the particles, 40% or more; more preferably 45% or more. Preferably, the amount of fatty acid in the particles is, by weight based on the weight of the particles, 95% or less; more preferably less than 90%; more preferably 85% or less.

In the particles, the weight ratio of fatty amide to fatty acid is 0.12:1 or higher; preferably 0.18:1 or higher. In the particles the weight ratio of fatty amide to fatty acid is 2.3:1 or lower; preferably 1.5:1 or lower; more preferably 1.2:1 or lower.

Preferably, the $R^1$ group of the fatty acid (as defined above) is an unsubstituted hydrocarbon group having 8 or more carbon atoms; more preferably 14 or more carbon atoms; more preferably 18 or more carbon atoms; more preferably 20 or more carbon atoms. Preferably, the $R^1$ group of the fatty acid is a hydrocarbon group having 30 or fewer carbon atoms; more preferably 25 or fewer carbon atoms. Preferably, the $R^1$ group of the fatty acid is a hydrocarbon group having one or two carbon-carbon double bonds. Preferably, the fatty acid is erucic acid.

Preferably, some or all of the fatty acid is in the carboxylate form. Preferably, the mole % of the fatty acid that is in carboxylate form is 50%-100%; more preferably 75%-100%.

In some embodiments, one or more surfactant is also present in the dispersion. Preferred are anionic and nonionic surfactants. More preferred are nonionic surfactants. Preferred nonionic surfactants are block copolymer surfactants and ethoxylated fatty compound surfactants. Ethoxylated fatty compound surfactants are surfactants that have a molecule that contains the structure —$(OCH_2CH_2)_n$— and that contains an unsubstituted hydrocarbon group; preferably n is 3 or more; more preferably n is 5 or more; preferably the hydrocarbon group has 8 or more carbon atoms; more preferably 12 or more carbon atoms; more preferably 16 or more carbon atoms.

When one or more surfactant is present in the composition, the preferred amount of surfactant, by weight based on the total weight of the composition, is 5% or less; more preferably 4% or less; more preferably 3% or less. When one or more surfactant is present in the composition, the preferred amount of surfactant, by weight based on the total weight of the composition, is 0.1% or more; more preferably 0.2% or more.

The present invention also involves a method of making the composition described herein. The method of the present invention includes the step of applying shear to a mixture that comprises said fatty amide, said fatty acid, and water, wherein said applying shear is performed at a temperature above 59° C., and wherein the amount of water in said mixture is 30% or less by weight based on the weight of said mixture.

The method of the present invention preferably involves making a high internal phase emulsion (HIP emulsion), which is defined herein as an emulsion in which the dispersed phase constitutes 30% or more by weight of the emulsion based on the weight of the emulsion. In preferred HIP emulsions, the amount of dispersed phase, by weight based on the weight of the emulsion, is 50% or more; more preferably 70% or more. To produce an HIP emulsion, a mixture (I) is made that contains water, fatty amide, fatty acid, neutralizing agent, optional surfactant, and optional additional ingredients.

Preferably, in mixture (I), the weight ratio of fatty amide to fatty acid is 2.3:1 or lower; more preferably 1.5:1 or lower; more preferably 1.2:1 or lower. Preferably, in mixture (I), the weight ratio of fatty amide to fatty acid is 0.12:1 or higher; more preferably 0.18:1 or higher.

In mixture (I), the amount of water, by weight based on the weight of mixture (I) is preferably 70% or less; more preferably 50% or less; more preferably 30% or less; more preferably 20% or less; more preferably 15% or less. Preferably, in mixture (I), the amount of water, by weight based on the weight of mixture (I) is 1% or more; more preferably 2% or more.

In mixture (I), preferred neutralizing agents are inorganic bases and organic bases. Among organic bases, organic amines are preferred. Inorganic bases are preferred. Preferred inorganic bases are hydroxide compounds; more preferred are sodium hydroxide, potassium hydroxide, and ammonium hydroxide; more preferred are potassium hydroxide and ammonium hydroxide.

In mixture (I), the amount of neutralizing agent is characterized by the equivalent ratio, which is defined herein as the ratio of equivalents of neutralizing agent to the equivalents of fatty acid. Preferably, the equivalent ratio in mixture (I) is 1.2:1 or lower; more preferably 1.01:1 or lower. Preferably, the equivalent ratio in mixture (I) is 0.5:1 or higher; more preferably 0.6:1 or higher; more preferably 0.7:1 or higher.

Preferably, one or more surfactant is included in mixture (I). Preferred surfactants and preferred amounts for mixture (I) are the same as those described herein above regarding the composition of the present invention.

Preferably, shear is applied to mixture (I) by use of a mechanical agitator. Preferably, the mechanical agitator provides uniform mixing, which means that every portion of mixture (I) is exposed to shear and that the various ingredients of mixture (I) are intimately mixed. It is contemplated that the amount of water in mixture (I) is relatively low compared to typical mixtures that are intended to produce emulsions; therefore it is contemplated that the viscosity of mixture (I) will be high compared to the viscosity of typical mixtures that are intended to produce emulsions, and so it is contemplated that the mechanical agitator must have sufficient power to provide uniform mixing in such a mixture.

Preferred mechanical agitators are melt kneaders, rotating-blade mixers, and rotor-stator mixers. Among melt kneaders, preferred are kneaders, Banbury™ mixers, single-screw extruders, and twin-screw extruders. Preferred rotating-blade mixers operate at rotation rates of 500 rpm or higher. Preferred rotating-blade mixers have toothed blades like, for example, Cowles-type blades.

Shear is applied to mixture (I) while mixture (I) is at a temperature of 59° C. or higher. Preferably, if the melting point of the fatty acid is above 59° C., shear is applied to mixture (I) at a temperature that is above the melting point of the fatty acid. Preferably, if mixture (I) has a single melting point, shear is applied to mixture (I) while mixture (I) is at a temperature above the melting point of mixture (I).

If mixture (I) is exposed to temperature of 100° C. or higher, preferably mixture (I) is kept in a container that is closed and can contain pressure above 1 atmosphere, so that the water in mixture (I) remains in the liquid state.

Preferably, the result of applying shear to mixture (I) is that mixture (I) becomes an HIP emulsion. Preferably the particle size distribution of the dispersed particles has the characteristics described herein above for the particle size distribution in the composition of the present invention.

After formation of the HIP emulsion, the composition is preferably cooled to room temperature.

Optionally, after formation of the HIP emulsion, the HIP is diluted by addition of water or other aqueous medium. It is contemplated that both the HIP and the composition formed by the dilution process are compositions of the present invention.

It is contemplated that cooling to room temperature and adding additional water do not change the particles sizes of the dispersed particles.

Preferably, the composition of the present invention is a stable dispersion. A dispersion is herein considered stable if the dispersion can be stored at 25° C. without any significant settling, creaming, other sign of phase separation, change in particle size, or change in viscosity. Viscosity is measured at 25° C. using a Brookfield viscometer. A significant change in viscosity is a change of 25% or more, based on the initial viscosity. A significant change in particle size is a change of 50% or more of the median diameter, based on the initial median diameter. Preferably, the composition of the present invention is stable for 1 day or more; more preferably 3 days or more; more preferably 1 month or more; more preferably 6 months or more.

The following are examples of the present invention.

Compositions were made using one of the preparation methods ("Prep Meth") 1 or 2 as follows.

Preparation method 1 was as follows. Erucamide, erucic acid, potassium hydroxide (or ammonium hydroxide), and water (mixture (I) for this method) were placed in a 300 mL Parr reactor vessel fitted with a Cowles blade. The material was heated to 100° C. while mixing slowly. Once the set temperature was reached, the mixer was run on high speed (approximately 1800 rpm) for 25 minutes. While still mixing on high, the sample was diluted to a desired concentration with water ("initial water") fed into the reactor with an HPLC pump at a rate of 20 mL/min Heat was removed and stirring continued until the temperature cooled to 45° C. or lower. The Parr was then opened and the dispersion was collected. In some cases, the resulting mixture was mixed with additional water ("dilution water").

Preparation method 2 was as follows. Preparation method 2 was as follows. The erucamide (Armoslip E from Akzo Nobel) and erucic acid (Prifrac 2990 from Croda) were blended together with surfactant at 60-80° C. on a rotovap system. The heated blend was transferred to a heated feed tank. The heated blend is pumped at a rate of 15 grams/minute into a rotor stator mixer. A 28 percent (weight/weight) solution of ammonium hydroxide solution was fed along with additional water into the rotor stator mixer to create the emulsified mixture product. Rates for the two streams can be found in Tables below. The mixer speed was set at approximately 700 rpm. In some cases the emulsified mixture product was collected as the inventive dispersion. As needed, the emulsified mixture could be fed into a second rotor stator mixer along with additional water to create the inventive dispersion. The second mixer speed could be set at approximately 500 rpm. The volume average particle size diameter of the solid content of the dispersion was measured and results are shown in Tables below.

Particle sizes were determined using a Coulter LS™ 13-320 Particle Size Analyzer (Beckman Coulter, Inc.) with a Universal Liquid Module as the sample delivery system. The system conforms to the ISO 13-320 standard. The software version utilized was Version 6.01. The analysis conditions for all measurements used a fluid refractive index of 1.332, a sample real refractive index of 1.5, and a sample imaginary refractive index of 0.0. The polarization intensity differential scattering (PIDS) option was activated and used to generate the particle size information. The volume average particle size diameter was measured and reported in μm.

A Coulter LATRON™ 300 LS latex standard was used to calibrate the particle size analyzer.

The following compositions were made. Each was judged according to whether an acceptable dispersion was produced. In order to be considered acceptable, the dispersion had to have median particle size of 50 micrometer or smaller; to be free of visible individual particles, and to be stable. Stable dispersions were acceptable upon making and remained so for at least 3 days of storage at room temperature.

The following surfactants were used:
Dowfax™ 2A1 surfactant=alkyldiphenyloxide disulfonate (Dow Chemical Co.)
Pluronic™ F-108 surfactant=ethylene oxide/propylene oxide block copolymer (BASF)
Tergitol™ 15-S-30 surfactant=secondary alcohol ethoxylate, (Dow Chemical Co.)
Serdox™ NXC6 surfactant=oleic acid monoethalolamide+6EO (Elementis Specialties, Inc.)
Neodol™ 23-6-6.5 surfactant=C12-C13 alcohol with approximately 6.5 moles of ethylene oxide per mole of alcohol (Shell Chemicals)
Brij™ 700 surfactant=ethoxylated fatty alcohol (Croda)

In each of the following compositions mixture (I) was formed by mixing erucamide with one or more of water, component 2 ("C2"), surfactant 1 ("S1"), and surfactant 2 ("S2") as shown in the table below. "Ex." is "Example; "E/C2" is the weight ratio of erucamide to C2; "PS" is particle size in micrometers; "U" denotes an unacceptable dispersion. Example numbers that contain "C" denote comparative examples. When a fatty acid is listed as a salt, the fatty acid was 100 mole % in the carboxylate form unless otherwise noted.

| | Ex 146C | Ex 150C | Ex 151C | Ex 152C | Ex 153C |
|---|---|---|---|---|---|
| Prep Meth | 1 | 1 | 1 | 1 | 1 |
| erucamide (g) | 22.35 | 30.24 | 30.22 | 12.65 | 10.35 |
| C2 | none | none | none | none | none |
| E/C2 | 100/0 | 100/0 | 100/0 | 100/0 | 100/0 |
| S1 type | Dowfax 2A1 | oleic acid K+ salt | oleic acid K+ salt | oleic acid K+ salt | oleic acid K+ salt |
| S1 (g) | 0.48 | 2.28 | 2.24 | 1.02 | 0.79 |
| S2 type | Pluronic F-108 | Tergitol 15-S-30 | Pluronic F-108 | none | Pluronic F-108 |
| S2 (g) | 0.5 | 0.93 | 0.92 | 0 | 0.32 |
| initial water (g) | 11.08 | 11.1 | 11.33 | 237 | 189 |
| dilution water (g) | 200 | 200 | 200 | 0 | 0 |
| PS | U | U | U | U | U |
| note | (1) | (1) | (1) | (2) | (2) |

Note (1): Too high an amount of erucamide; unacceptable dispersion despite the use of various surfactants
Note (2): Too high an amount of erucamide; unacceptable dispersion despite the use of surfactant and large amounts of water

| | Ex 187 | Ex 189 | Ex 190 | Ex 193 | Ex 194 |
|---|---|---|---|---|---|
| PrepMeth | 1 | 1 | 1 | 1 | 1 |
| erucamide (g) | 5.35 | 8.73 | 20.27 | 10.17 | 10.69 |
| C2 | erucic acid, K+ salt | erucic acid, K+ salt | erucic acid, K+ salt | erucic acid, ammonium salt | erucic acid, ammonium salt |
| E/C2 | 20/80 | 30/701 | 50/50 | 30/70 | 30/70 |
| S1 type | none | none | none | none | none |
| S2 type | none | none | none | none | none |
| initial water (g) | 12.12 | 11.78 | 13.22 | 27.14 | 16.48 |
| dilution water (g) | 200 | 200 | 200 | 200 | 200 |

-continued

|        | Ex 187 | Ex 189 | Ex 190 | Ex 193 | Ex 194 |
|--------|--------|--------|--------|--------|--------|
| PS     | 0.15   | 0.21   | 2.7    | 2.9    | 3.7    |
| note   |        |        |        |        | (3)    |

Note (3): erucic acid was partially neutralized; 80 mole % of the acid groups were in carboxylate form; it is contemplated that this allows for the use of an unusually small amount of water.

|              | Ex 230C | Ex 231C | Ex 232C | Ex 236C | Ex 237C | Ex. 238C |
|--------------|---------|---------|---------|---------|---------|----------|
| Prep Meth    | 1       | 1       | 1       | 1       | 1       | 1        |
| erucamide (g)| 14.31   | 14.15   | 14.18   | 18.27   | 16.01   | 14.15    |
| C2           | Erucic acid, K+ salt | Erucic acid, K+ salt | Erucic acid, K+ salt | Erucic acid, K+ salt | Erucic acid, K+ salt | Erucic acid, ammonium salt |
| E/C2         | 70/30   | 70/30   | 70/30   | 89/11   | 80/20   | 70/30    |
| S1 type      | Serdox NXC6 | Serdox NXC6 | Serdox NXC6 | Serdox NXC6 | Serdox NXC6 | Serdox NXC6 |
| S1 (g)       | 0.97    | 1.01    | 1       | 1.16    | 1.02    | 0.93     |
| S2 type      | Neodol 23-6.5 | additional Serdox NXC6 | Brij 700 | none | none | none |
| S2 (g)       | 19.06   | 3.22    | 7.4     | 0       | 0       | 0        |
| initial water (g) | 12.94 | 13.46 | 13.2 | 9.68 | 10.22 | 11.54 |
| dilution water (g) | 200 | 200 | 200 | 200 | 200 | 200 |
| PS           | U       | U       | U       | U       | U       | U        |
| note         | (5)     | (5)     | (5)     | (5)     | (5)     | (5)      |

Note (5): Too high an amount of erucamide; unacceptable dispersion

|              | Ex 239  | Ex 240  | Ex 242  |
|--------------|---------|---------|---------|
| Prep Meth    | 1       | 1       | 1       |
| erucamide (g)| 6.07    | 6.03    | 6.08    |
| C2           | Erucic acid, ammonium salt | Erucic acid, ammonium salt | Erucic acid, ammonium salt |
| E/C2         | 30/70   | 30/70   | 30/70   |
| S1 type      | Serdox NCX6 | Serdox NCX6 | Pluronic F-108 |
| S1 (g)       | 0.96    | 1.03    | 0.99    |
| S2 type      | none    | none    | none    |
| initial water (g) | 11.06 | 9.23 | 10.18 |
| dilution water (g) | 200 | 200 | 200 |
| PS           | (6)     | 1.3     | 0.98    |

Note (6): visual inspection showed that the dispersion was acceptable; particle size was not measured.

Examples 187, 189, 190, 193, 194, 239, 240, and 242 were stored at room temperature (approximately 25° C.) for 6 months and were observed to be stable dispersions at that time.

|              | Ex 1001 | Ex 1002 | Ex 1003 | Ex 1004 |
|--------------|---------|---------|---------|---------|
| Prep Meth    | 2       | 2       | 2       | 2       |
| C2           | Erucic acid | Erucic acid | Erucic acid | Erucic acid |
| E/C2         | 80/20   | 70/30   | 50/50   | 30/70   |
| S1 type      | Pluronic F-108 | Pluronic F-108 | Pluronic F-108 | Pluronic F-108 |
| S1/E         | 14/86   | 14/86   | 14/86   | 14/86   |
| Aq. ammonia solution rate (g/min) | 0.54 | 2.05 | 1.0 | 2.05 |
| Initial water rate (g/min) | 40 | 30 | 40 | 38 |
| Second water rate (g/min) | none | None | none | none |
| PS (μm)      | 22.2    | 0.12    | 0.14    | 0.15    |

Examples 1001, 1002, 1003, and 1004 were stored for 1 month at room temperature (approximately 25° C.) and were observed to be stable dispersions.

The invention claimed is:

1. A composition comprising dispersed particles in an aqueous medium, wherein said dispersed particles comprise one or more fatty amide and one or more fatty acid, wherein 50 mole % or more of said fatty acid in is the carboxylate form, and wherein the weight ratio of said fatty amide to said fatty acid is from 0.12:1 to 2.3:1,
wherein said dispersed particles constitute 30% or more by weight based on the weight of said composition and wherein said fatty amide has the chemical formula $R^2$—C(O)$NHR^3$, wherein $R^2$ is a substituted or unsubstituted hydrocarbyl group that contains 8 or more carbon atoms, and wherein $R^3$ is selected from the following:
(I) $R^3$ is hydrogen
(II) $R^3$ is an aliphatic unsubstituted hydrocarbyl group, or
(III) $R^3$ has the structure —$CH_2CH_2$—NHC(O)—$R^4$, where $R^4$ is a substituted or unsubstituted hydrocarbyl group that contains 8 or more carbon atoms.

2. The composition of claim 1, wherein said fatty amide is erucamide.

3. The composition of claim 1, wherein the weight ratio of said fatty amide to said fatty acid is from 0.18:1 to 1.2:1.

4. The composition of claim 1, wherein the median size of said particles is 50 micrometer or smaller.

5. The composition of claim 1, wherein 75 mole % or more of said fatty acid in is the carboxylate form.

6. A method of making the composition of claim 1, comprising the step of applying shear to a mixture that comprises said fatty amide, said fatty acid, and water, wherein said applying shear is performed at a temperature above 59° C., and wherein the amount of water in said mixture is 70% or less by weight based on the weight of said mixture.

7. The method of claim 6, wherein said fatty amide is erucamide.

8. The method of claim 6, wherein the amount of water in said mixture is 12% or less by weight based on the weight of said mixture.

9. The method of claim 6, wherein said mixture further comprises one or more neutralizing agent, and wherein the ratio of equivalents of said neutralizing agent to equivalents of said fatty acid is from 0.5:1 to 1.01:1.

10. The method of claim 6, wherein the weight ratio of fatty amide to fatty acid is 0.18:1 to 1.2:1.

11. The method of claim 6, wherein said applying shear to said mixture is performed at a temperature above the melting point of said fatty acid.

12. The composition of claim 1, wherein said dispersed particles constitute 50% or more by weight based on the weight of said composition.

13. The composition of claim 1, wherein said dispersed particles constitute 70% or more by weight based on the weight of said composition.

14. The composition of claim 1, wherein the amount of fatty amide in said particles is 10% or more by weight based on the weight of said particles, and wherein the amount of fatty acid in said particles is 40% or more by weight based on the weight of said particles.

15. The composition of claim 1, wherein said fatty acid has structure $R^1$—COOH or $R^1$—COO$^\ominus$, wherein $R^1$ is a hydrocarbon group having 20 or more carbon atoms, and wherein said fatty amide has structure $R^2$—C(O)NH$_2$, wherein $R^2$ is a hydrocarbon group having 20 or more carbon atoms.

16. The composition of claim 1, wherein the fatty acid is erucic acid.

17. The method of claim 6, wherein said dispersed particles constitute 70% or more by weight based on the weight of said composition.

18. The method of claim 6, wherein the amount of fatty amide in said particles is 10% or more by weight based on the weight of said particles, and wherein the amount of fatty acid in said particles is 40% or more by weight based on the weight of said particles.

19. The method of claim 6, wherein said fatty acid has structure $R^1$—COOH or $R^1$—COO$^\ominus$, wherein $R^1$ is a hydrocarbon group having 20 or more carbon atoms, and wherein said fatty amide has structure $R^2$—C(O)NH$_2$, wherein $R^2$ is a hydrocarbon group having 20 or more carbon atoms.

20. The composition of claim 1, further comprising one or more nonionic surfactant.

\* \* \* \* \*